(12) United States Patent
Rubinfeld et al.

(10) Patent No.: US 9,555,111 B2
(45) Date of Patent: Jan. 31, 2017

(54) OCULAR CROSS-LINKING SYSTEM AND METHOD FOR SEALING CORNEAL WOUNDS (71) Applicants: CXL Ophthalmics, LLC, Encinitas, CA (US); Brad Hartman, Renton, WA (US)

(72) Inventors: Roy S. Rubinfeld, Bethesda, MD (US); Raymond A. Hartman, Carlsbad, CA (US); Sandy T. Feldman, Del Mar, CA (US)

(73) Assignee: CXL Ophthalmics, LLC, Encinitas, CA (US)

( * ) Notice: Subject to any disclaimer, the term of this patent is extended or adjusted under 35 U.S.C. 154(b) by 0 days.

(21) Appl. No.: 14/387,532

(22) PCT Filed: Mar. 27, 2013

(86) PCT No.: PCT/US2013/034185
§ 371 (c)(1),
(2) Date: Sep. 23, 2014

(87) PCT Pub. No.: WO2013/148895
PCT Pub. Date: Oct. 3, 2013

(65) Prior Publication Data
US 2015/0126921 A1    May 7, 2015

Related U.S. Application Data (60) Provisional application No. 61/617,326, filed on Mar. 29, 2012.

(51) Int. Cl.
A61K 41/00    (2006.01)
A61K 9/00     (2006.01)
(Continued)

(52) U.S. Cl.
CPC .......... *A61K 41/0057* (2013.01); *A61F 9/008* (2013.01); *A61F 9/0079* (2013.01); *A61K 9/0048* (2013.01);
(Continued)

(58) Field of Classification Search
CPC .... A61F 9/0079; A61F 9/008; A61K 49/0015; A61K 38/44; A61K 41/0057; A61K 9/0048; A61K 31/525; A61K 41/00; A61N 5/062
(Continued)

(56) References Cited

U.S. PATENT DOCUMENTS 3,132,068 A    5/1964   Behrman
4,676,790 A    6/1987   Kern
(Continued)

FOREIGN PATENT DOCUMENTS

CA    2319087 A1    8/1999
CA    2418306 A1    1/2002
(Continued)

OTHER PUBLICATIONS

Wollensak et al. "Corneal Endothelial Cytotoxicity of Riboflavin/UVA Treatment in vitro." Ophthalmic Res. 35:324-328, 2003.
(Continued)

*Primary Examiner* — Lynsey Crandall
*Assistant Examiner* — Dacheng Xie
(74) *Attorney, Agent, or Firm* — Procopio, Cory, Hargreaves & Savitch, LLP (57) ABSTRACT Wounds in the eye following surgery or injury are sealed by soaking the area with a riboflavin solution containing iodide ion and irradiating the wound area with UVA radiation in a selected wavelength range for a selected time period to
(Continued)

promote cross-linking of tissue between opposite surfaces of the wound or between the incised wound surfaces and a graft or implant.

12 Claims, 4 Drawing Sheets

(51) Int. Cl.
| | |
|---|---|
| A61N 5/06 | (2006.01) |
| A61F 9/007 | (2006.01) |
| A61F 9/008 | (2006.01) |
| A61K 31/525 | (2006.01) |
| A61K 33/18 | (2006.01) |
| A61K 38/44 | (2006.01) |
| A61B 18/00 | (2006.01) |
| A61N 5/067 | (2006.01) |

(52) U.S. Cl.
CPC ............ *A61K 31/525* (2013.01); *A61K 33/18* (2013.01); *A61K 38/44* (2013.01); *A61K 41/00* (2013.01); *A61N 5/062* (2013.01); *A61B 2018/0063* (2013.01); *A61B 2018/00619* (2013.01); *A61F 2009/00865* (2013.01); *A61F 2009/00872* (2013.01); *A61N 2005/063* (2013.01); *A61N 2005/067* (2013.01); *A61N 2005/0626* (2013.01); *A61N 2005/0661* (2013.01); *A61N 2005/0662* (2013.01); *A61N 2005/0663* (2013.01); *A61N 2005/0667* (2013.01); *C12Y 111/01006* (2013.01)

(58) Field of Classification Search
USPC .............................. 606/4; 424/9.6, 94.4, 671
See application file for complete search history.

(56) References Cited

U.S. PATENT DOCUMENTS

| | | | |
|---|---|---|---|
| 4,863,627 A | 9/1989 | Davies et al. | |
| 5,368,590 A | 11/1994 | Itoh | |
| 5,639,481 A | 6/1997 | Kessler | |
| 5,849,291 A | 12/1998 | Kessler | |
| 6,043,237 A * | 3/2000 | Meadows | A61K 41/0071 514/185 |
| 6,099,521 A | 8/2000 | Shadduck | |
| 6,161,544 A | 12/2000 | DeVore et al. | |
| 6,162,210 A | 12/2000 | Shadduck | |
| 6,183,086 B1 | 2/2001 | Neubert | |
| 6,248,335 B1 | 6/2001 | Duan et al. | |
| 6,309,656 B1 | 10/2001 | Pugliese et al. | |
| 6,413,268 B1 | 7/2002 | Hartman | |
| 6,447,537 B1 | 9/2002 | Hartman | |
| 6,471,691 B1 | 10/2002 | Kobayashi | |
| 6,544,286 B1 | 4/2003 | Perez | |
| 6,783,539 B1 | 8/2004 | Timberlake | |
| 6,880,558 B2 | 4/2005 | Perez | |
| 7,015,252 B2 | 3/2006 | Fujii et al. | |
| 7,044,945 B2 | 5/2006 | Sand | |
| 7,073,510 B2 | 7/2006 | Redmond | |
| 7,077,839 B2 | 7/2006 | Hamblin | |
| 7,186,417 B1 * | 3/2007 | Siegel | A61K 9/0034 424/405 |
| 7,220,278 B2 | 5/2007 | Peyman | |
| 7,288,106 B2 | 10/2007 | Heacock | |
| 7,331,350 B2 | 2/2008 | Kochevar | |
| 7,479,136 B2 | 1/2009 | Dotson | |
| 7,498,156 B2 | 3/2009 | Goodrich | |
| 7,727,544 B2 | 6/2010 | Schwartz | |
| 7,744,590 B2 | 6/2010 | Eells | |
| 7,753,943 B2 | 7/2010 | Strong | |
| 7,943,590 B2 | 5/2011 | Flugelman | |
| 8,034,373 B2 | 10/2011 | Reynolds et al. | |
| 8,092,490 B2 | 1/2012 | Redmond et al. | |
| 8,100,530 B2 | 1/2012 | Zhou et al. | |
| 8,106,038 B2 | 1/2012 | Margaron et al. | |
| 8,177,778 B2 | 5/2012 | Muller et al. | |
| 8,215,314 B2 | 7/2012 | Chan et al. | |
| 8,238,993 B2 | 8/2012 | Maynard et al. | |
| 8,398,628 B2 | 3/2013 | Muller | |
| 8,574,277 B2 | 11/2013 | Muller et al. | |
| 8,580,789 B2 | 11/2013 | Krueger et al. | |
| 9,125,856 B1 | 9/2015 | Paik et al. | |
| 2001/0016731 A1 | 8/2001 | Devore et al. | |
| 2002/0006394 A1 | 1/2002 | Redmond | |
| 2002/0013577 A1 | 1/2002 | Frey et al. | |
| 2002/0022606 A1 | 2/2002 | Kochevar | |
| 2003/0083649 A1 | 5/2003 | Margaron | |
| 2003/0105521 A1 | 6/2003 | Perez | |
| 2003/0175259 A1 | 9/2003 | Karageozian et al. | |
| 2003/0208190 A1 | 11/2003 | Roberts et al. | |
| 2004/0137068 A1 | 7/2004 | Bhushan | |
| 2005/0070942 A1 | 3/2005 | Perez | |
| 2005/0124982 A1 | 6/2005 | Perez | |
| 2005/0149006 A1 | 7/2005 | Peyman | |
| 2005/0152993 A1 | 7/2005 | De Oliveira | |
| 2005/0241653 A1 | 11/2005 | Heugten et al. | |
| 2005/0271590 A1 | 12/2005 | Schwartz et al. | |
| 2005/0283234 A1 | 12/2005 | Zhou et al. | |
| 2006/0074487 A1 | 4/2006 | Gilg | |
| 2006/0084951 A1 | 4/2006 | Heacock | |
| 2006/0134170 A1 | 6/2006 | Griffith et al. | |
| 2006/0166879 A1 | 7/2006 | Bhushan et al. | |
| 2006/0172972 A1 | 8/2006 | Bhushan et al. | |
| 2006/0177430 A1 | 8/2006 | Bhushan et al. | |
| 2006/0235513 A1 | 10/2006 | Price, Jr. | |
| 2006/0268231 A1 | 11/2006 | Gil et al. | |
| 2006/0275278 A1 | 12/2006 | Choy et al. | |
| 2007/0088415 A1 | 4/2007 | Peyman | |
| 2007/0128174 A1 | 6/2007 | Kleinsek et al. | |
| 2007/0129286 A1 | 6/2007 | Zhang | |
| 2007/0135805 A1 | 6/2007 | Peyman | |
| 2007/0142828 A1 | 6/2007 | Peyman | |
| 2007/0167935 A1 | 7/2007 | Serdarevic | |
| 2007/0207116 A1 | 9/2007 | Brown | |
| 2007/0225778 A1 | 9/2007 | Heacock | |
| 2008/0009901 A1 | 1/2008 | Redmond | |
| 2008/0015660 A1 | 1/2008 | Herekar | |
| 2008/0039769 A1 | 2/2008 | Peyman | |
| 2008/0057023 A1 | 3/2008 | Chynn | |
| 2008/0097174 A1 | 4/2008 | Maynard et al. | |
| 2008/0114283 A1 | 5/2008 | Mattson | |
| 2008/0139671 A1 | 6/2008 | Herekar | |
| 2008/0161780 A1 | 7/2008 | Serdarevic | |
| 2008/0208177 A1 | 8/2008 | Mrochen et al. | |
| 2008/0246920 A1 | 10/2008 | Buczek et al. | |
| 2008/0269119 A1 | 10/2008 | Griffith et al. | |
| 2008/0269730 A1 | 10/2008 | Dotson | |
| 2008/0288063 A1 | 11/2008 | Price, Jr. | |
| 2009/0099557 A1 | 4/2009 | Sedarevic | |
| 2009/0105127 A1 | 4/2009 | Thompson | |
| 2009/0149842 A1 | 6/2009 | Muller et al. | |
| 2009/0149923 A1 | 6/2009 | Herekar | |
| 2009/0171305 A1 | 7/2009 | El Hage | |
| 2009/0192437 A1 | 7/2009 | Soltz | |
| 2009/0275929 A1 | 11/2009 | Zickler | |
| 2010/0057059 A1 | 3/2010 | Makino | |
| 2010/0057060 A1 | 3/2010 | Herekar | |
| 2010/0069894 A1 | 3/2010 | Mrochen | |
| 2010/0087920 A1 | 4/2010 | Marmo | |
| 2010/0114109 A1 | 5/2010 | Peyman | |
| 2010/0173019 A1 | 7/2010 | Palk et al. | |
| 2010/0189817 A1 | 7/2010 | Krueger et al. | |
| 2010/0210996 A1 | 8/2010 | Peyman | |
| 2010/0286156 A1 | 11/2010 | Pinelli | |
| 2010/0318017 A1 | 12/2010 | Lewis et al. | |
| 2011/0060129 A1 | 3/2011 | Akashi et al. | |
| 2011/0060267 A1 | 3/2011 | DeWoolfson et al. | |
| 2011/0081323 A1 | 4/2011 | Kleinsek et al. | |
| 2011/0086802 A1 | 4/2011 | Dewoolfson et al. | |
| 2011/0118654 A1 | 5/2011 | Muller et al. | |
| 2011/0125187 A1 | 5/2011 | Soltz et al. | |
| 2011/0149247 A1 | 6/2011 | Artsyukhovich | |

(56) References Cited

U.S. PATENT DOCUMENTS

| | | |
|---|---|---|
| 2011/0160710 A1 | 6/2011 | Frey et al. |
| 2011/0237999 A1 | 9/2011 | Muller et al. |
| 2011/0264082 A1 | 10/2011 | Mrochen et al. |
| 2011/0282333 A1 | 11/2011 | Herekar et al. |
| 2011/0288466 A1 | 11/2011 | Muller et al. |
| 2011/0301524 A1 | 12/2011 | Bueler et al. |
| 2011/0306956 A1 | 12/2011 | Islam |
| 2012/0059439 A1 | 3/2012 | Yoon |
| 2012/0065572 A1 | 3/2012 | Lewis et al. |
| 2012/0083772 A1 | 4/2012 | Rubinfeld et al. |
| 2012/0095455 A1 | 4/2012 | Rodmond et al. |
| 2012/0121567 A1 | 5/2012 | Troisi et al. |
| 2012/0203161 A1 | 8/2012 | Herekar |
| 2012/0215155 A1 | 8/2012 | Muller et al. |
| 2012/0238938 A1 | 9/2012 | Herekar et al. |
| 2012/0283531 A1 | 11/2012 | Maynard et al. |
| 2012/0283621 A1 | 11/2012 | Muller |
| 2012/0289886 A1 | 11/2012 | Muller et al. |
| 2012/0310083 A1 | 12/2012 | Friedman et al. |
| 2012/0310141 A1 | 12/2012 | Kornfield et al. |
| 2013/0060187 A1 | 3/2013 | Friedman et al. |
| 2013/0079759 A1 | 3/2013 | Dotson et al. |
| 2013/0085370 A1 | 4/2013 | Friedman et al. |
| 2013/0158342 A1 | 6/2013 | Chan et al. |
| 2013/0245536 A1 | 9/2013 | Friedman et al. |

FOREIGN PATENT DOCUMENTS

| | | | |
|---|---|---|---|
| CA | 2473703 A1 | 7/2003 | |
| CA | 2511217 A1 | 7/2004 | |
| CA | 2515720 A1 | 9/2004 | |
| CA | 2566961 A1 | 12/2005 | |
| CA | 2576308 A1 | 2/2006 | |
| CA | 2577025 A1 | 2/2006 | |
| CA | 2700884 A1 | 2/2009 | |
| JP | 54101440 | 8/1979 | |
| RU | 1803110 A1 | 3/1993 | |
| SK | WO 03068247 A1 * | 8/2003 | ............ A61K 33/18 |
| WO | 0182933 A2 | 11/2001 | |
| WO | 03061518 A2 | 7/2003 | |
| WO | 03068247 A1 | 8/2003 | |
| WO | 2004024035 A1 | 3/2004 | |
| WO | 2005117987 A1 | 12/2005 | |
| WO | 2007011874 A2 | 1/2007 | |
| WO | 2007011875 A2 | 1/2007 | |
| WO | 2007020673 A2 | 2/2007 | |
| WO | 2007026382 A1 | 3/2007 | |
| WO | 2007035843 A2 | 3/2007 | |
| WO | 2007082127 A2 | 7/2007 | |
| WO | 2008005059 A2 | 1/2008 | |
| WO | 2008055118 A2 | 5/2008 | |
| WO | 2009001396 A1 | 12/2008 | |
| WO | 2009146151 A2 | 12/2009 | |
| WO | 2010023705 A1 | 3/2010 | |
| WO | 2010093908 A2 | 8/2010 | |
| WO | 2011011202 A1 | 2/2011 | |
| WO | 2011019940 A2 | 2/2011 | |
| WO | 2011041437 A1 | 4/2011 | |
| WO | 2011050164 A1 | 4/2011 | |
| WO | 2011056477 A1 | 5/2011 | |
| WO | 2011109712 A2 | 9/2011 | |
| WO | 2011152861 A2 | 12/2011 | |
| WO | 2012035403 A1 | 3/2012 | |
| WO | 2012047307 A1 | 4/2012 | |
| WO | 2013148896 A1 | 10/2013 | |

OTHER PUBLICATIONS

Wollensak et al. "Endothelial cell damage after riboflavin-ultraviolet-A treatment in the rabbit." J Cataract Refract Surg. 29:1786-1790, 2003.

Wollensak et al. "Keratocyte Apoptosis After Corneal Collagen Cross-linking Using Riboflavin/UVA Treatment." Cornea. 23(1):43-49, Jan. 2004.

Wollensak et al. "Keratocyte cytotoxicity of riboflavin/UVA treatment in vitro." Eye. 2004, in 5 pages.

EMX Industries, Inc.; ColorMax HEX Color Sensors; Mar. 2010.

Wells et al. "Oxidative Stress in Developmental Origins of Disease: Teratogenesis, Neurodevelopmental Deficits, and Cancer." Toxicological Sciences. 108(1):4-18 (2009).

Uttara et al. "Oxidative Stress and Neurodegenerative Diseases: A Review of Upstream and Downstream Antioxidant Therapeutic Options." Current Neuropharmacology. 7:65-74 (2009).

Sukkar et al. "Oxidative stress and nutritional prevention in autoimmune rheumatic diseases." Autoimmunity Reviews. 3:199-206 (2004).

Bickers et al. "Oxidative Stress in the Pathogenesis of Skin Disease." The Society for Investigative Dermatology. pp. 2565-2575, 2006.

Gilgun-Sherki et al. "Oxidative stress induced-neurodegenerative diseases: the need for antioxidants that penetrate the blood brain barrier." Neuropharmacology. 40:959-975 (2001).

Oduntan et al. "A review of the role of oxidative stress in the pathogenesis of eye diseases." S Afr Optom. 70(4):191-199 (2011).

Kato et al. "Topography-Guided Conductive Keratoplasty: Treatment for Advanced Keratoconus." American Journal of Ophthalmology. 150(4):481-489 (Oct. 2010).

Kohnen et al. "Bewertung und Qualitätssicherung refraktivchirurgischer Eingriffe durch die DOG und den BVA (Evaluation and quality assurance of refractive surgery by the German Ophthalmological Society and the Professional Association of German Ophthalmologists)." Ophthalmologie. 108(9):869-882 (Sep. 2011). Available only in German.

Wollensak et al. "Long-term biomechanical properties of rabbis cornea after photodynamic collagen crosslinking." Acta Ophthalmologica. 87:48-51, 2009.

Kullman. "Alternative Applications of the Femtosecond Laser in Ophthalmology." Seminars in Ophthalmology. 25(5-6):256-264 (Nov. 2010).

Chuo et al. "Modern Corneal and Refractive Procedures." Expert Review of Ophthalmology. 6(2):247-266 (Apr. 2011).

Epstein."Refraktive Chirurgie." Therapeutische Umschau. Revue Therapeutique. 66(3):207-210 (Mar. 2009). English abstract.

Wollensak et al. "Riboflavin/Ultraviolet-A-induced Collagen Crosslinking for the Treatment of Keratoconus." Am J Ophthalmol. 135:620-627, 2003.

Wollensak et al. "Wound Healing in the Rabbit Cornea After Corneal Collagen Cross-Linking With Riboflavin and UVA." Cornea. 26:600-605, 2007.

Wollensak et al. "Stress-strain measurements of human and porcine corneas after riboflavin-ultraviolet-A-induced cross-linking." J Cataract Refract Surg. 29:1780-1785, 2003.

Wollensak et al. "Collagen Fiber Diameter in the Rabbit Cornea After Collagen Crosslinking by Riboflavin/UVA." Cornea. 23(5):503-507, Jul. 2004.

International Search Report and Written Opinion for related international application No. PCT/US2013/034185, mailed Jul. 11, 2013, in 12 pages.

International Preliminary Report on Patentability for PCT/US2013/034185, mailed on Oct. 1, 2014, in 7 pages.

Wollensak et al., "Cross-linking of scleral collagen in the rabbit using riboflavin and UVA", ACTA Ophthalmologica Scandinavica, 2005, vol. 83, pp. 477-482.

International Search Report and Written Opinion for related international application No. PCT/US2013/034467 mailed on Jul. 26, 2013 in 12 pages.

Agbor, et al. "Effect of Iodine Supplementation on Antioxidant Status of Normal and Alloxan Monohydrate in Toxicated Rats", International Journal of Pharmacology, 7 (6): pp. 726-731, 2011, Asian Network for Scientific Information.

Rieger, et al. "The Effect of Iodide Iontophoresis on the Antioxidative Capacity of the Tear Fluid" Graefe's Archive or Clinical Experimental Ophthalmology. 248:1639-1646 (2010).

(56) References Cited

OTHER PUBLICATIONS

Rieger, "Anti-oxidative Capacity of Various Artificial Tear Preparations", Graefe's Arch. Clin. Exp. Opthalmol., 2001, vol. 239, pp. 222-226.
El-Raggal, "Riboflavin-Ultraviolet a Corneal Cross linking for Keratoconus", Middle East African Journal of Opthalmology, Oct.-Dec. 2009; 16(4): 256-259, 8 pages.
Supplementary European Search Report for EP 13767439.6 mailed on Sep. 15, 2015 in 6 pages.
Rose, R.C. et al.: "Ocular oxidants and antioxidant protection", Experimental Biology and Medicine, vol. 217, No. 4, 1998, pp. 397-407.
Beijing Yasi Technology and Development Co., Ltd."Eye sponge product information",Jul. 29, 2011.
Ibusuki et al.: "Photochemically Cross-Linked Collagen Gels as Three-Dimensional Scaffolds for Tissue Engineering", Tissue Engineering, vol. 13, No. 8, Aug. 14, 2007, pp. 1995-2001.
Horwath-Winter J, et al: "Iodide iontophoresis as a treatment for dry eye syndrome", The British Journal of Ophthalmology, Jan. 2005, pp. 40-44, vol. 89, No. 1.
Singh et al: "Clinical Evaluation of Sodium Iodide in the Treatement of Various Types of Cataracts", Journal of the Indian Medical Association, 1983, pp. 119-121, vol. 81, No. 7-8.
Winkler et al: "Effect of Iodide on Total Antioxidant Status of Human Serum", Cell Biochemistry and Function, Jun. 2000, pp. 143-146, vol. 18, No. 2.
Partial supplementary European Search Report for EP 13768403.1 mailed on Oct. 23, 2015 in 10 pages.
Ilens Ophthalmic Solution, http://naikutty.in/medicine-list-i/article/86937-ilens-solution, Date unknown but available prior to the date of this application.
Baert et al (Medical Radiology: Diagnostic Imaging, Radiological Imaging of the Ureter, copyright 2003, Springer).
Abraxis (Iodopen MSDS, Revision date of Jun. 13, 2006).
Bessonova et al. "A study of the stability of eye drops containing riboflavine (Russian)." XP002719481. Database accession No. EMB-1978057912. Abstract. Database EMBase (Online). Elsevier Science Publishers, Amsterdam, NL, 1977.
Elstner et al. "Uptake and biochemical Activity of Potassium Iodide in Isolated Rabbit Eyes." XP008167001. Ophtlalmologica. 191(2):122-126 (1985). English abstract provided.
Koltun et al. "Improving the production technology of vitamin-containing eye drops to ensure their microbiological purity." XP002719482. Database accession No. PREV199497454025. Abstract. Database BIOSIS (Online). Biosciences Information Service, Philadelphia, PA, US, 1993.
Rieger. "Anti-oxidative capacity of various artificial tear preparations." XP003014992. Graefe's Archive for Clinical Experimental Ophthalmology. 239:222-226 (2001).
Schmut et al. "Iodide protection from UVB irradiation-induced degradation of hyaluronate and against UVB-damage of human conjunctival fibroblasts." XP008166988. Graefe's Archive for Clinical Experimental Ophthalmology. 242(4):279-283 (2004).
Shimmura et al. "Subthreshold UV Radiation-induced Peroxide Formation in Cultured Corneal Epithelial Cells: The Protective Effects of Lactoferrin." XP055098621. Experimental Eye Research. 63(5):519-526 (1996).
Ishimitsu et al. "The photochemical decomposition and hydroxylation of phenylalanine in the presence of riboflavin." XP008167014. Chemical and Pharmaceutical Bulletin, Pharmaceutical Society of Japan. 33(4):1552-1556 (1985).
Zhang et al. "Clinical effect of traditional Chinese herb combined with sodium iodide in treating corneal opacity." XP002719483. Database accession No. EMB-2007125131. Database EMBase (Online). Elsevier Science Publishers, Amsterdam, NL, Feb. 2007.
Extended European Search Report mailed on Feb. 10, 2014 for related EP Patent Application No. 11831060 in 15 pages.
Cho et al. "Reactive Oxygen Species-Induced Apoptosis and Necrosis in Bovine Corneal Endothelial Cells." Investigative Ophthalmology & Visual Science. 40(5):911-919, Apr. 1999.
Fujimori. "Cross-linking and fluorescence changes of collagen by glycation and oxidation." Biochimica et Biophysica Acta. 998:105-110, 1989.
Hull et al. "Hydrogen Peroxide-Mediated Corneal Endothelial Damage." Investigative Ophthalmology & Visual Science. 25:1246-1253, 1984.
Iseli et al. "Efficacy and Safety of Blue-light Scleral Cross-linking." International Congress of Corneal Cross-Linking, Dec. 7-8, 2007; Zurich, Switzerland. pp. S752-S755.
Khadem et al. "Photodynamic Biologic Tissue Glue." Cornea. 13(5):406-410, 1994.
Kohlhaas et al. "Biomechanical evidence of the distribution of cross-links in corneas treated with riboflavin and ultraviolet a light." J Cataract Refract Surg. 32:279-283, Feb. 2006.
Krueger et al. "Rapid vs Standard Collagen CXL with Equivalent Energy Dosing." Third International Congress of Corneal Crosslinking. Dec. 7-8, 2007; Zurich, Switzerland, in 25 pages.
Sato et al. "The Primary Cytotoxicity in Ultraviolet-A-Irradiated Riboflavin Solution is Derived from Hydrogen Peroxide." The Society for Investigative Dermatology, Inc. 105(4):608-612, Oct. 1995.
Seiler et al. "Corneal Cross-Linking-Induced Stromal Demarcation Line." Clinical Science. 25(9):1057-1059, Oct. 2006.
Spoerl et al. "Increased resistance of crosslinked cornea against enzymatic digestion." Current Eye Research. 29(1):35-40, 2004.
Spoerl et al. "Induction of Cross-links in Corneal Tissue." Exp. Eye Res. 66:97-103, 1998.
Spoerl et al. "Safety of UVA-Riboflavin Cross-Linking of the Cornea." Cornea. 26(4):385-389, May 2007.
Spoerl et al. "Thermomechanical Behavior of Collagen-Cross-Linked Porcine Cornea." Ophthalmologica. 218:136-140, 2004.
International Search Report and Written Opinion for related international application No. PCT/US2013/033923, mailed Jul. 12, 2013, in 13 pages.
International Search Report and Written Opinion PCT/US2011/033873 mailed Jan. 17, 2012 in 14 pages.

* cited by examiner

OCULAR CROSS-LINKING SYSTEM AND METHOD FOR SEALING CORNEAL WOUNDS

CROSS-REFERENCE

This application claims priority to U.S. Provisional Application No. 61/617,326, filed Mar. 29, 2012, which is incorporated herein by reference in its entirety.

BACKGROUND

Collagen cross-linking is a parasurgical treatment for multiple ophthalmic disorders. In some cases, collagen cross-linking may also be combined with other treatments to improve corneal strength or optical refraction. Treatment methods include mini asymmetric radial keratotomy, corneal ring segment inserts, or topography-guided laser. Corrective lenses are normally required after these treatments, but with smaller, more normalized prescriptions. Increased corneal symmetry allows for more comfortable contact lens wear, often of daily disposable lenses. Collagen crosslinking limits deterioration of vision, increases unaided and uncorrected vision, and may reduce the need for corneal transplantation.

SUMMARY

Disclosed herein, in certain embodiments, is a method for sealing wounds in an eye of a patient following surgery or injury, the method comprising: (a) applying a riboflavin solution to a wound area; and (b) irradiating the wound area with UVA or UVA/blue radiation in a predetermined wavelength range for a predetermined time period. In some embodiments, applying the riboflavin solution comprises soaking the wound area with the riboflavin solution. In some embodiments, the riboflavin solution comprises iodide ion or catalase enzyme. In some embodiments, the riboflavin solution comprises 0.001% to 6.0% by weight sodium iodide. In some embodiments, the iodide is kept in ionized (I—) form by suitable control of a basic solution to a pH of 7.0 to 8.4. In some embodiments, irradiating the wound area with UVA radiation promotes cross-linking of tissue between opposite surfaces of the wound area or between incised wound surfaces and a graft or implant. In some embodiments, the riboflavin solution comprises up to 10% by weight riboflavin. In some embodiments, the riboflavin solution comprises a diluted fibrinogen or fibrin glue. In some embodiments, the riboflavin solution further comprises a dilute sugar. In some embodiments, the dilute sugar comprises 1-4 diaminobutane or hexamethylene. In some embodiments, the UVA or UVA/blue radiation is in a wavelength range from 320 nm to 500 nm. In some embodiments, the UVA radiation is in a wavelength range from 330 nm to 380 nm. In some embodiments, the blue radiation is in a wavelength range from 400 to 470 nm. In some embodiments, the UVA or UVA/blue radiation is in a wavelength range from 400 to 410 nm. In some embodiments, the selected time period is in a range from around five to ten minutes. In some embodiments, the UVA radiation has a predetermined intensity in a range from 1.0 to 40 mw/cm$^2$. In some embodiments, the UVA radiation has a predetermined intensity in a range from 1.0 to 5 mw/cm$^2$.

Disclosed herein, in certain embodiments, is an ocular wound sealing system, the system comprising: (a) a photosensitizer solution comprising (i) riboflavin, and (ii) iodide ion, catalase, or a combination thereof; (b) a light source having an output in a selected UVA or UVA/blue or blue light range. In some embodiments, the system further comprises an adjustable optical treatment head, the treatment head comprising an optical projector defining an optical axis and configured to project a beam of light in a predetermined UVA or UVA/blue or blue light range along the optical axis to a wound area of the eye. In some embodiments, the system further comprises a positioning control element for adjusting distance from the eye and the orientation of the optical axis relative to an axis of the eye. In some embodiments, the system further comprises a beam intensity adjustment module for adjusting the light intensity incident on the wound area. In some embodiments, the system further comprises a control module for controlling a treatment time period. In some embodiments, the adjustable optical treatment head is adjustable in at least one of an x-axis, a y-axis, and a z-axis. In some embodiments, the riboflavin solution comprises 0.001% to 6.0% by weight sodium iodide. In some embodiments, the iodide is kept in ionized (I—) form by suitable control of a basic solution to a pH of about 7.0 to about 8.4. In some embodiments, the riboflavin solution comprises up to about 10% by weight riboflavin. In some embodiments, the riboflavin solution further comprises a diluted fibrinogen or fibrin glue. In some embodiments, the riboflavin solution further comprises a dilute sugar. In some embodiments, the dilute sugar comprises 1-4 diaminobutane or hexamethylene. In some embodiments, the UVA or UVA/blue radiation is in a wavelength range from 320 nm to 500 nm. In some embodiments, the UVA radiation is in a wavelength range from 330 nm to 380 nm. In some embodiments, the UVA/blue radiation is in a wavelength range from 400 to 470 nm. In some embodiments, the UVA or UVA/blue radiation is in a wavelength range from 400 to 410 nm.

Disclosed herein, in some embodiments, are methods of sealing wounds in the eye following surgery or injury, comprising: (a) applying a riboflavin solution to at least the wound area; and (b) irradiating the wound area with UVA radiation in a predetermined wavelength range for a selected time period.

In some embodiments, applying the riboflavin solution comprises soaking the wound area with a riboflavin solution. In some embodiments, the riboflavin solution comprises an iodide ion. In some embodiments, irradiating the wound area with UVA radiation in a predetermined wavelength range for a selected time period comprises promoting cross-linking of tissue between opposite surfaces of the wound or between the incised wound surfaces and a graft or implant. In some embodiments, riboflavin acts as a photosensitizer. In some embodiments, the iodide ion releases oxygen for cross-linking. In some embodiments, UVA light together with the photosensitizer produce cross-linking to seal or weld the wound in the illuminated tissue area.

In some embodiments, the riboflavin solution comprises about 0.01% to about 20% by weight riboflavin. In some embodiments, the riboflavin solution comprises up to and including about 20%, 19%, 18%, 17%, 16%, 15%, 14%, 13%, 12%, 11%, 10% or less by weight riboflavin. In some embodiments, the riboflavin solution comprises up to and including about 10%, 9.75%, 9.5%, 9.25%, 9%, 8.75%, 8.5%, 8.25%, 8%, 7.75%, 7.5%, 7.25%, 7%, 6.75%, 6.5%, 6.25%, 6% or less by weight riboflavin. In some embodiments, the riboflavin solution comprises up to 10% by weight riboflavin. In some embodiments, the riboflavin solution comprises at least about 0.01%, 0.02%, 0.03%, 0.04%, 0.05%, 0.06%, 0.07%, 0.085, 0.09%, 0.10%, 0.20%, 0.30%, 0.40%, 0.50%. 0.60%, 0.70%, 0.80%, 0.90%, 1%, 1.25%, 1.5%, 1.75%, 2%, 2.25%, 2.5%, 2.75%, 3% or more by weight riboflavin. In some embodiments, the riboflavin solution further comprises one or more additional components. In some embodiments, the one or more additional components increase cross-linking. In some embodiments, the one or more additional components are selected from the group comprising iodide ion or catalase enzyme. In some embodiments, the riboflavin solution comprises 0.001% to 6.0% by weight sodium iodide. In some embodiments, the iodide is kept in the ionized (I⁻) form by suitable control of the basic solution to a pH of 7.0 to 8.4 with no acids or other oxidizing agents. In some embodiments, the one or more additional components enhance the bond. In some embodiments, the riboflavin solution further comprises a diluted fibrinogen glue.

In some embodiments, the predetermined wavelength range is between about 330 nm to about 380 nm. In some embodiments, the predetermined wavelength range is between about 340 nm to about 375 nm. In some embodiments, the predetermined wavelength range is between about 350 to about 375 nm. In some embodiments, the predetermined wavelength range is between about 360 nm to 370 nm.

In some embodiments, the selected period time is between about 1 to about 30 minutes. In some embodiments, the selected period time is between about 1 to about 20 minutes. In some embodiments, the selected period time is between about three to about seventeen minutes. In some embodiments, the selected period time is between about five minutes to about fifteen minutes. In some embodiments, the selected period of time is between about five to about ten minutes. In some embodiments, the selected period time is between about five minutes to about eight minutes. In some embodiments, the selected period time is greater than or equal to about 2, 3, 4, 5, 6, 7, 8, 9, 10 or more minutes. In some embodiments, the selected period of time is less than or equal to about 25, 20, 19, 18, 17, 16, 15, 14, 13, 12, 11 or fewer minutes.

In some embodiments, irradiating the wound area with UVA radiation comprises a predetermined UVA intensity. In some embodiments, the predetermined UVA intensity is between about 1.0 to about 40.0 mw/cm². In some embodiments, the UVA radiation has a predetermined intensity in a range from 1.0 to 5 mw/cm². In some embodiments, the predetermined UVA intensity is between about 2.0 to about 8.0 mw/cm². In some embodiments, the predetermined UVA intensity is between about 2.0 to about 5.0 mw/cm². In some embodiments, the predetermined UVA intensity is between about 3.0 to about 5.0 mw/cm². In some embodiments, the predetermined UVA intensity is between about 3.0 to about 8.0 mw/cm². In some embodiments, the predetermined UVA intensity is greater than or equal to about 1.0, 1.5, 2.0, 2.5, 3.0, 3.5, 4.0, 4.5, 5, 10, 15, 20, 25, 30, 35, 40 or more mw/cm². In some embodiments, the predetermined UVA intensity is less than or equal to about 10.0, 9.5, 9.0, 8.5, 8.0, 7.5, 7.0, 6.5, 6.0, 5.5, 5.0 or fewer mw/cm².

In some embodiments, the wound area comprises an incident surface of the eye. In some embodiments, the dose or energy per unit area applied at the incident surface of the eye is between about 0.1 to about 5 J/cm². In some embodiments, the dose applied at the incident surface of the eye is between about 0.2 to about 4.5 J/cm². In some embodiments, the dose applied at the incident surface of the eye is between about 0.3 to about 4 J/cm². In some embodiments, the dose applied at the incident surface of the eye is between about 0.4 to about 3 J/cm². In some embodiments, the dose applied at the incident surface of the eye is between about 0.5 to about 2 J/cm². In some embodiments, the dose applied at the incident surface of the eye is between about 0.5 to about 1 J/cm². In some embodiments, the dose applied at the incident surface of the eye is less than or equal to about 2, 1.5, 1.4, 1.3, 1.2, 1.1, 1, 0.9, 0.8, 0.7 or fewer J/cm². In some embodiments, the dose applied at the incident surface of the eye is greater than or equal to about 0.1, 0.2, 0.3, 0.4, 0.5, 0.6, 0.7, 0.8, 0.9 or more J/cm².

In some embodiments, the UVA intensity is 3.0 mw/cm². In some embodiments, the predetermined time period is five minutes. In some embodiments, the dose applied at the incident surface of the eye is 0.9 J/cm².

Further disclosed herein, in some embodiments, are ocular wound sealing systems, comprising (a) a supply of photosensitizer solution containing riboflavin and iodide ion; (b) a light source having an output in a selected UVA or blue light range; (c) an x, y, z adjustable optical treatment head configured to receive the output of the light source; (d) a positioning control system for adjusting the distance of the treatment head from the eye and the orientation of the optical axis relative to the eye axis; (e) a beam intensity adjustment module for adjusting the light intensity incident on the wounded area of the eye; and (f) an on-off control module for controlling the treatment time period. In some embodiments, the photosensitizer solution is applied to an eye. In some embodiments, the treatment head comprises an optical projection system defining an optical axis and configured to project a beam of light in a predetermined UVA wavelength range along the optical axis onto an eye area including a surgical or traumatic wound.

In some embodiments, the ocular wound sealing methods and/or systems are used for sealing wounds in the cornea or sclera. In some embodiments, the ocular wound sealing methods and/or systems are used for sealing wounds in the corneal cataract incisions, corneal or scleral lacerations (trauma), relaxing incisions and other surgical wounds resulting from surgery to adjust refractive properties of the cornea, flaps or other corneal surgeries or treatments, other refractive surgeries, scleral incisions, and keratoplasties. In some embodiments, corneal surgeries or treatments comprise LASIK.

Other features and advantages of the present disclosure will become more readily apparent to those of ordinary skill in the art after reviewing the following detailed description and accompanying drawings.

BRIEF DESCRIPTION OF THE DRAWINGS

The details of the present disclosure, both as to its structure and operation, may be gleaned in part by study of the accompanying drawings, in which like reference numerals refer to like parts, and in which.

DETAILED DESCRIPTION

Certain embodiments as disclosed herein provide methods and systems for sealing wounds in the eye resulting from surgery or trauma. For example, one method for sealing wounds as disclosed herein comprises (a) applying a topical solution comprising riboflavin and at least one additional photosensitizer or cross-linking enhancing component to the eye or to a predetermined wound area in the eye; and (b) applying a treatment beam of UVA radiation of predetermined wavelength or wavelength range to at least the wound area for a selected time period and beam intensity so as to promote cross-linking at the wound site for wound sealing purposes.

After reading this description it will become apparent to one skilled in the art how to implement the devices and methods of the disclosure in various alternative embodiments and alternative applications. However, although various embodiments of the present disclosure will be described herein, it is understood that these embodiments are presented by way of example only, and are not limiting. As such, the detailed description of various alternative embodiments should not be construed to limit the scope or breadth of the present disclosure as set forth in the appended claims.

In some embodiments, the wound sealing systems and methods described herein are used for sealing one or more types of surgical or traumatic wound in the cornea or sclera of the eye, including corneal cataract incisions, corneal and scleral lacerations, relaxing incisions or other incisions for adjusting refractive properties of the cornea, corneal flaps following LASIK or other refractive surgeries, scleral incisions, and keratoplasties.

Figure 1:
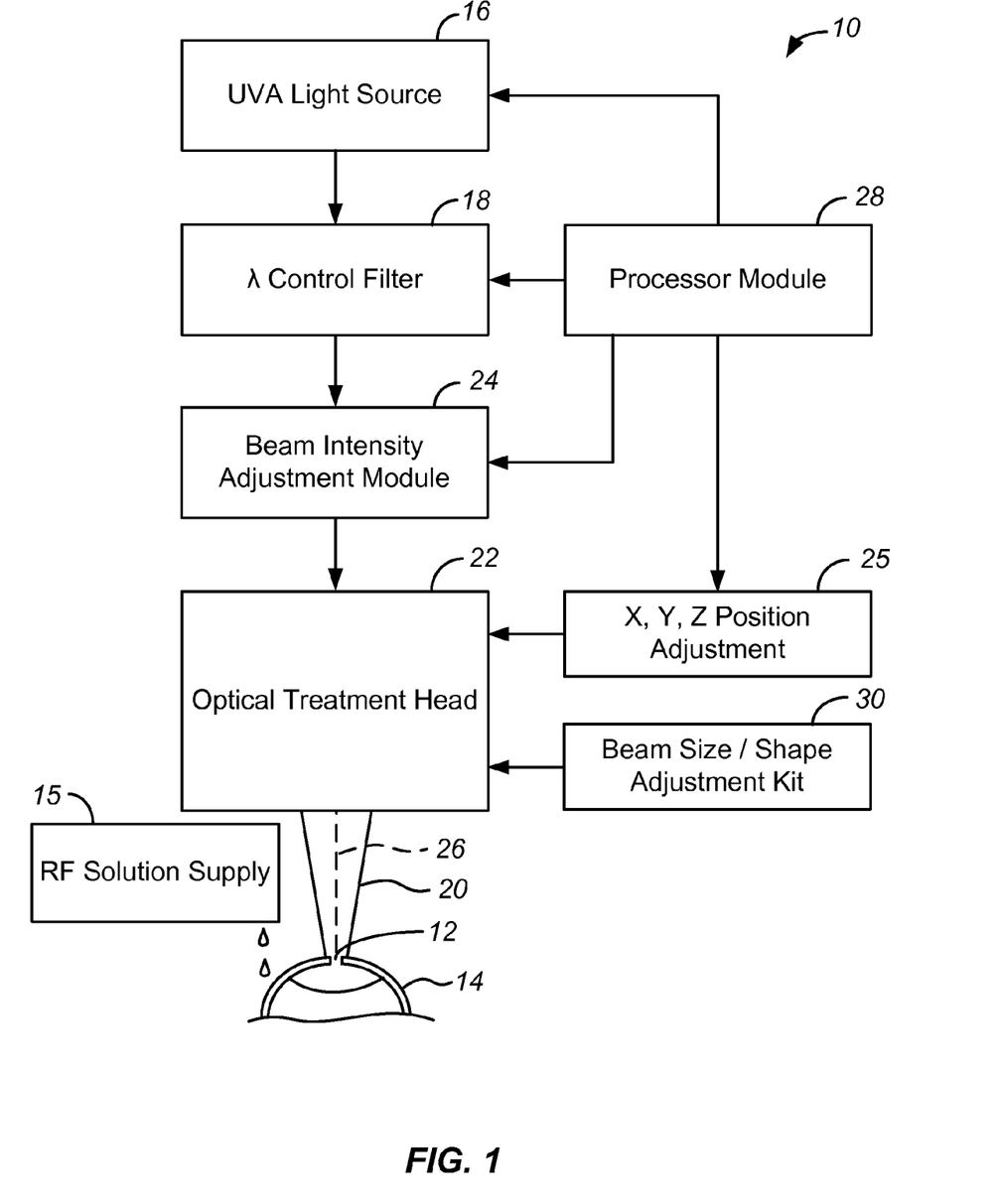
FIG. 1 is an exemplary block diagram of an ocular wound sealing treatment system for applying light in a predetermined wavelength range to seal a wound in the cornea or sclera according to some embodiments of the disclosure.

FIG. 1 is a block diagram of a phototherapy treatment system 10 for providing a UVA treatment light beam 20 directed at a wound area 12 in the eye 14, together with a riboflavin solution supply 15 for applying drops of solution to the eye prior to irradiation with the UVA beam. In some embodiments, the phototherapy treatment system 10 comprises a light beam 20. In some embodiments, the phototherapy system 10 comprises a riboflavin solution supply 15. In some embodiments, the phototherapy treatment system comprises a light source 16. In some embodiments, light source 16 comprises a UVA light source. In some embodiments, the UVA light source is a laser diode or light emitting diode, or a UVA lamp. In some embodiments, the light source 16 comprises a multi-spectral light source. In some embodiments, the multi-spectral light source is a short arc mercury or mercury halide lamp, or a xenon lamp. In some embodiments, the phototherapy system 10 comprises a wavelength control filter 18. In some embodiments, the phototherapy system 10 comprises an optical treatment head 22. In some embodiments, the phototherapy system comprises a beam intensity adjustment module 24. In some embodiments, the wavelength control filter 18 controls the wavelength of light transmitted to the optical treatment head 22, and the beam intensity adjustment module 24 controls the light beam intensity to provide a selected radiation dose at the irradiated area of the eye 14. In some embodiments, the phototherapy system 10 comprises an x, y, z adjustment device 25. In some embodiments, the phototherapy system 10 comprises a treatment beam axis 26. In some embodiments, the x, y, z adjustment device 25 provides horizontal and vertical control of the position of the optical treatment head 22 relative the eye 14 as well as well as angular positioning of the optical treatment head 22 relative to the eye 14. In some embodiments, the treatment beam axis 26 is centered on the desired wound area and oriented to be directed substantially perpendicular to the wound area. In some embodiments, the adjustment is manual. For example, manual adjustment comprises vertical and/or horizontal slide positioning of the optical treatment head 22, and adjustment of a swivel joint mount of the optical treatment head 22, prior to locking each adjuster in position. In some embodiments, the phototherapy system 10 comprises a processor module 28. In some embodiments, the processor module 28 comprises a control unit. In some embodiments, the control unit enables entry of positioning commands. In some embodiments, the positioning is controlled by a processor module 28 having a control unit for manual entry of positioning commands.

In some embodiments, the phototherapy system 10 further comprises a beam size and shape adjustment kit 30. In some embodiments, the kit 30 comprises a plurality of different masks, plastic slides, reticules or a combination thereof. In some embodiments, the plurality of masks, plastic slides, reticules or combination thereof allow selectively position in the light path through optical treatment head 22.

Figure 2:
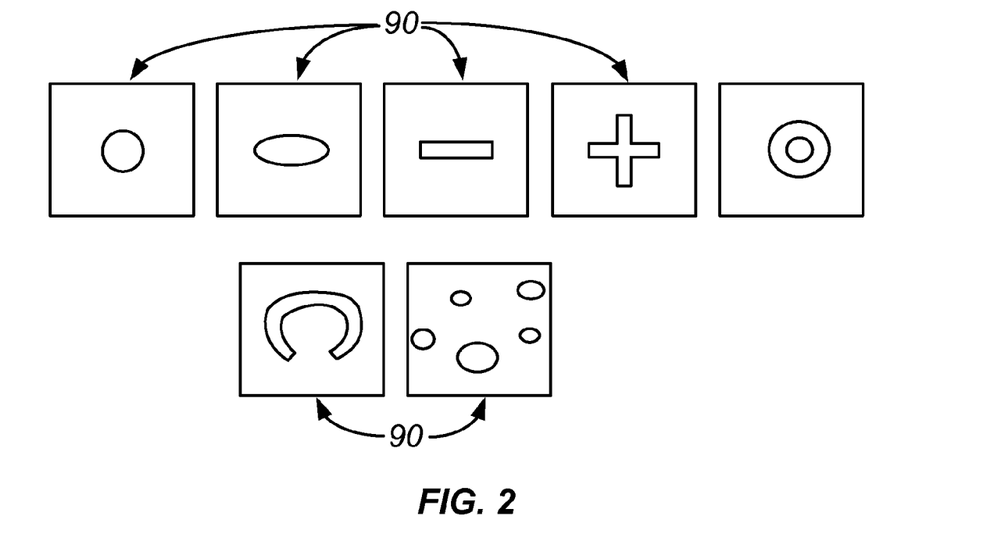
FIG. 2 illustrates some examples of optical slides or reticules with various aperture shapes and sizes for controlling the shape and size of the treatment beam in the embodiment of FIG. 1.

FIG. 2 illustrates some examples of possible slides 90 with different opening shapes. In some embodiments, as shown in FIG. 2, the opening shapes are round, oval, and rectangular. In some embodiments, the different shapes comprise a "+", donut or "C" shape. In some embodiments, the different shapes comprise one or more circles. In some embodiments, the different openings of sizes and shapes correspond to typical eye surgical wound areas.

In some embodiments, prior to treatment of the wound area with UVA radiation, a riboflavin based photosensitizer solution 15 is applied to the wound. In some embodiments, a topical solution comprising about 0.1 wt. % to about 10 wt. % riboflavin and about 0.001 wt. % to about 6.0 wt % sodium iodide in a hypotonic or aqueous solution is applied to the wound area and allowed to soak into the eye for a selected time period. In some embodiments, the solution comprises around about 0.5 wt. % riboflavin and about 0.015 wt. % to 5 wt. % sodium iodide.

In some embodiments, the solution comprises about 0.001 wt. % to about 20 wt. % sodium iodide. In some embodiments, the solution comprises up to and including about 20 wt. %, 19 wt. %, 18 wt. %, 17 wt. %, 16 wt. %, 15 wt. %, 14 wt. %, 13 wt. %, 12 wt. %, 11 wt. %, 10 wt. % or less sodium iodide. In some embodiments, the solution comprises up to and including about 10 wt. %, 9.75 wt. %, 9.5 wt. %, 9.25 wt. %, 9 wt. %, 8.75 wt. %, 8.5 wt. %, 8.25 wt. %, 8 wt. %, 7.75 wt. %, 7.5 wt. %, 7.25 wt. %, 7 wt. %, 6.75 wt. %, 6.5 wt. %, 6.25 wt. %, 6 wt. % or less sodium iodide. In some embodiments, the solution comprises up to 10 wt. % sodium iodide. In some embodiments, the solution comprises at least about 0.001 wt. %, 0.002 wt. %, 0.003 wt. %, 0.004 wt. %, 0.005 wt. %, 0.006 wt. %, 0.007 wt. %, 0.008 wt. %, 0.009 wt. %, 0.01 wt. %, 0.015 wt. %, 0.02 wt. %, 0.03 wt. %, 0.04 wt. %, 0.05 wt. %, 0.06 wt. %, 0.07 wt. %, 0.085, 0.09 wt. %, 0.10 wt. %, 0.20 wt. %, 0.30 wt. %, 0.40 wt. %, 0.50 wt. %. 0.60 wt. %, 0.70 wt. %, 0.80 wt. %, 0.90 wt. %, 1 wt. %, 1.25 wt. %, 1.5 wt. %, 1.75 wt. %, 2 wt. %, 2.25 wt. %, 2.5 wt %, 2.75 wt %, 3 wt % or more sodium iodide.

As used herein, the term "wt. %" refers to weight percent or percent by weight. In some embodiments the iodide is kept in the ionized (I—) form by control of the basic solution to a pH of 7.0 up to 8.4. In some embodiments, control of the basic solution does not comprise an acid or other oxidizing agent. In some embodiments, the solution further comprises one or more reducing agents. In some embodiments, the reducing agents comprise sodium thiosulfate, vitamin C, sodium bisulfate, or a combination thereof. In some embodiments, the one or more reducing agents are added to the solution. In some embodiments, the one or more reducing agents reduce the iodine formed back to iodide ions. In some embodiments, the solution comprises one or more additives. In some embodiments, the one or more additives are FDA approved non-active ingredients.

Figure 5A:
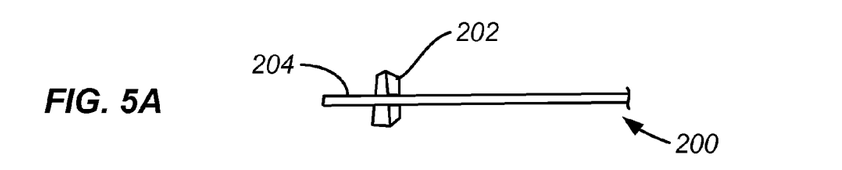
FIGS. 5A to 5C illustrates an exemplary micropipette syringe-like devices for adding small, measured amounts of treatment solution to a wound area in the eye according to some embodiments of the disclosure.
Figure 5B:
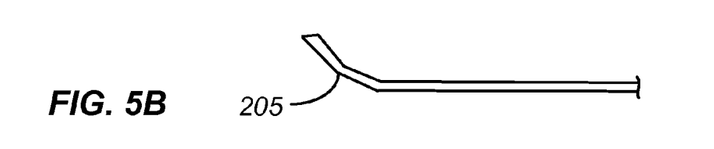
Figure 5C:
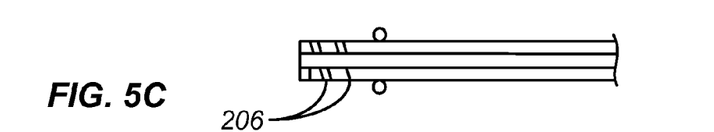
Figure 6:
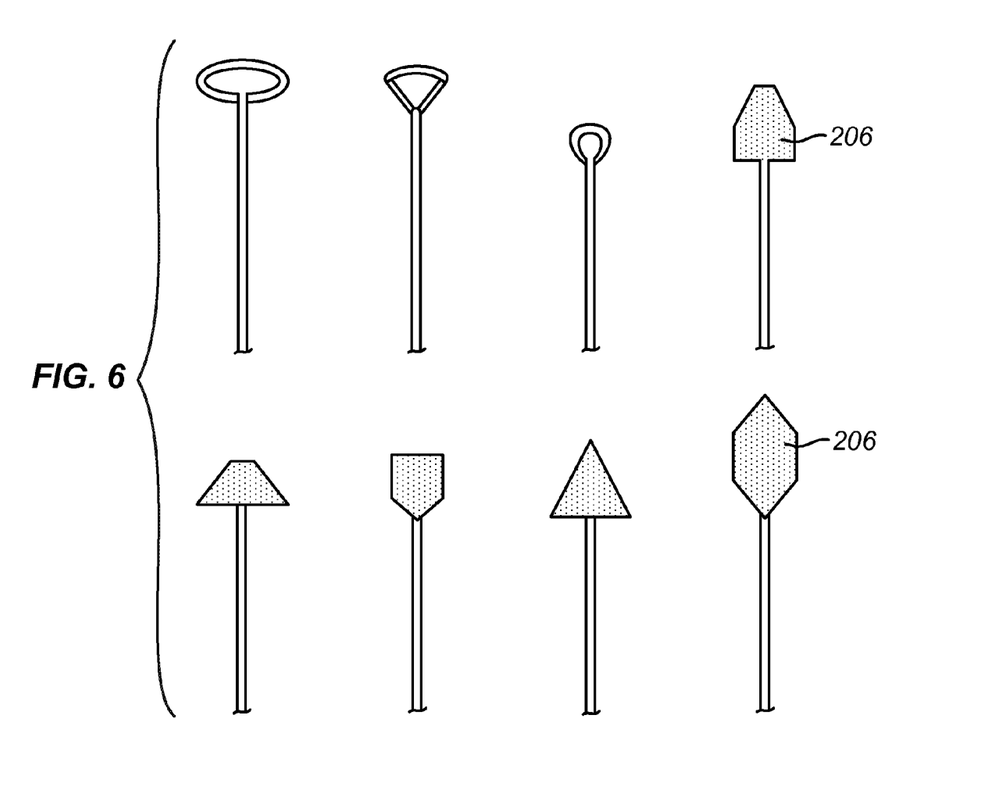
FIG. 6 illustrates some exemplary alternative drop insertion devices for various types of wounds.

In some embodiments, the amount of riboflavin applied to the wound is controlled. In some embodiments, controlling the amount of riboflavin avoids or reduces the risk of uneven wound sealing or welding. In some embodiments, controlling the amount of riboflavin prevents or reduces uneven wound sealing or welding. For example, one problem which arises in some cases in sealing flaps or other incisions after LASIK and other refractive surgery is that wrinkles on the eye surface form if too much riboflavin solution is loaded under or into the flap. Similar problems result in some cases in applying standard size drops of riboflavin to incisions or wounds. In some embodiments, a microdrop of around 0.1 to 0.5 the size of a standard eye drop is applied to the stromal bed of the cornea and not to the flap after flap surgery, or to the opposite sides of a corneal or scleral incision or wound. In some embodiments, a metered dropper is provided to supply drops of riboflavin solution in the range from around 1 to 50 microliters. In some embodiments, a metered dropper is provided to supply drops of riboflavin solution in the range from around 2 to 40 microliters. In some embodiments, a metered dropper is provided to supply drops of riboflavin solution in the range from around 2 to 30 microliters. In some embodiments, a metered dropper is provided to supply drops of riboflavin solution in the range from around 2 to 20 microliters. In some embodiments, a metered dropper is provided to supply drops of riboflavin solution in the range from around 2 to 15 microliters. In some embodiments, the drop size is less than or equal to 50, 47, 45, 42, 40, 37, 35, 32, 30, 27, 25, 22, 20 or fewer microliters. In some embodiments, the drop size is less than or equal to 35 microliters. In some embodiments, the drop size is greater than or equal to 1, 1.25, 1.5. 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10 or more microliters FIGS. 5 and 6 illustrate some alternative embodiments of micropipette syringe devices for instilling small, measured amounts of riboflavin solution or other treatment solutions into an ocular wound area. FIG. 5A illustrates the end of a tubular, generally straight micropipette device 200 of flexible, clear plastic material, with an inflatable cuff 202 from which the dispensing tip 204 of the device extends. The tip 205 of the micropipette syringe device is bent in FIG. 5B is bent for use in a tongue and groove type of surgical incision. FIG. 5C is an enlarged view of the device of FIG. 5A illustrating optional microperforations 206 in the tip of the device through which fluid is dispensed. In some embodiments, fluid is dispensed only through the open end of tip 204.

FIG. 6 illustrates multiple different shapes for the insertion tip of the device of FIG. 5, which is used in some cases instead of a short tubular tip 204 as in FIG. 5A for different types of wounds. These tips in some cases have multiple microperforations 206. In some embodiments, the shaft of the device is rigid, clear or transparent tube while the heads are of flexible tubing or the like.

In some embodiments, the tips described with reference to FIGS. 5 and 6 include a sponge. In some embodiments, the sponge comprises a PVA sponge. In some embodiments, the sponge absorbs excess riboflavin solution or other fluids. In some embodiments, the sponge prevents or reduces saturation of a corneal flap with riboflavin. In some embodiments, the sponge delivers fluids or solutions to the eye. In some embodiments, the sponge delivers fluids or solutions to a corneal flap, a corneal stroma bed, or other surgical wound. In some embodiments, a sterile sponge of PVA or other materials is used to ensure delivery of the fluids and solutions to the corneal flap or the corneal stroma bed or to other surgical wounds. In some embodiments, the fluids or solutions comprise a riboflavin solution.

In some embodiments, the riboflavin solution comprises one or more agents. In some embodiments, the one or more agents enhance the tissue bond by filling voids. In some embodiments, the one or more agents comprise a glue. In some embodiments, the one or more agents comprise a linking agent. In some embodiments, the riboflavin solution further comprises a diluted fibrinogen glue or a linking agent. In some embodiments, the glue is ineffective when used alone for long term sealing of corneal incisions. In some embodiments, addition of UVA phototherapy using riboflavin or riboflavin plus iodide ion solutions to the glue increases the strength of a seal. In some embodiments, addition of UVA phototherapy using riboflavin or riboflavin plus iodide ion solutions to the glue increases the tensile and/or shear strength of a seal. In some embodiments, addition of UVA phototherapy using a riboflavin solution increases the tensile and/or shear strength of a fibrinogen seal.

Another possible modification of the method disclosed herein when sealing a flap after LASIK or other refractive surgery is to pre-seal the edge of the flap with a fibrinogen glue after the riboflavin topical treatment and prior to UVA irradiation. In some embodiments, the method further comprises pre-sealing an edge of a flap with a glue. In some embodiments, pre-sealing the edge of the flap occurs prior to UVA irradiation. In some embodiments, pre-sealing the edge of the flap occurs after application of the riboflavin solution.

In some embodiments, the riboflavin solution further comprises one or more sugars. In some embodiments, the riboflavin solution further comprises one or more dilute sugars. In some embodiments, the one or more sugars enable void filling and/or cross-linking by glycation. In some embodiments, the riboflavin solution further comprises one or more linking agents. In some embodiments, the linking agent comprises 1-4 diaminobutane or hexamethylene. In some embodiments, the linking agent forms one or more dialdehydes. In some embodiments, the linking agent cross-links collagen fibrils to the amines or aldehydes on one or more collagen fibrils to form a permanent bridge.

In some embodiments, the method further comprises applying one or more solutions before, during or after UVA irradiation. In some embodiments, the method further comprises applying one or more topical solutions before, during or after UVA radiation. In some embodiments, the one or more solutions comprise a riboflavin solution. In some embodiments, the one or more solutions comprise a topical solution. In some embodiments, the one or more solutions comprise a photosensitizer solution. In some embodiments, the one or more topical solutions comprise a riboflavin solution. In some embodiments, the photosensitizer solution comprises a riboflavin solution. In some embodiments, the riboflavin solution further comprises an iodide ion. In some embodiments, the method further comprises applying one or more solutions before UVA irradiation. In some embodiments, the method further comprises applying one or more solutions one or more times before UVA irradiation. In some embodiments, the method further comprises applying one or more solutions 1, 2, 3, 4, 5, 6, 7, 8, 9, 10 or more times before UVA irradiation. In some embodiments, the one or more solutions are applied every 1, 2, 3, 4, 5, 6, 7, 8, 9, 10 or more minutes before UVA irradiation. In some embodiments, the method further comprises applying one or more solutions during UVA irradiation. In some embodiments, the method further comprises applying one or more solutions one or more times during UVA irradiation. In some embodiments, the method further comprises applying one or more solutions 1, 2, 3, 4, 5, 6, 7, 8, 9, 10 or more times during UVA irradiation. In some embodiments, the one or more solutions are applied every 1, 2, 3, 4, 5, 6, 7, 8, 9, 10 or more minutes during UVA irradiation. In some embodiments, the method further comprises applying one or more solutions after UVA irradiation. In some embodiments, the method further comprises applying one or more solutions one or more times after UVA irradiation. In some embodiments, the method further comprises applying one or more solutions 1, 2, 3, 4, 5, 6, 7, 8, 9, 10 or more times after UVA irradiation. In some embodiments, the one or more solutions are applied every 1, 2, 3, 4, 5, 6, 7, 8, 9, 10 or more minutes after UVA irradiation. In some embodiments, more topical solution is applied periodically during the UVA irradiation period. In some embodiments, the topical solution is applied periodically during the UVA irradiation every two to five minutes.

A monitoring system as described in co-pending patent application Ser. No. 13/034,488 filed on Feb. 24, 2011, the contents of which are incorporated herein by reference, is in some cases used to monitor the riboflavin amount in the eye during wound sealing photochemical treatment. In some embodiments, the phototherapy system further comprises a monitoring system. In some embodiments, the monitoring system monitors the amount of riboflavin in the eye. In some embodiments, the monitoring system monitors the amount of riboflavin in the eye during a wound sealing photochemical treatment. In some embodiments, the method further comprises monitoring the riboflavin amount in the eye. In some embodiments, measurement of riboflavin concentration allows the physician to monitor for excessive or insufficient riboflavin during the procedure and to take appropriate steps to mitigate such conditions. In some embodiments, the measurement of riboflavin concentration is based upon the detection of the photoluminescence of the riboflavin as it interacts with the excitation light. In some embodiments, the method further comprises applying the riboflavin solution based on the amount of riboflavin in the eye. In some embodiments, the method further comprises removing excess riboflavin in the eye. In some embodiments, removing excess riboflavin in the eye comprises absorbing the riboflavin. In some embodiments, absorbing the riboflavin comprises use of one or more sponges to absorb the riboflavin.

In some embodiments, the wound and adjacent areas of the eye are pre-treated by chemicals or scraping. In some embodiments, pretreatment allows riboflavin and iodide ions to readily penetrate into the wound and surrounding eye area for enhanced cross-linking. In some embodiments, the UVA radiation applied to the wound area is in a wavelength range from about 330 nm to about 380 nm. In some embodiments, UVA radiation applied to the wound area is in a wavelength range from about 360 to about 370 nm. In some embodiments, the wavelength range of the UVA radiation is obtained is by placing a UVA filter having an approximately 10 nm bandwidth at 365 nm in the light path to the optical treatment head. In some embodiments, different UVA filters have different wavelength bands. In some embodiments, different UVA filters with different wavelength bands allow selection of the wound sealing UVA treatment by placing different filters in the light path. In some embodiments, the UVA irradiation is applied for a time period in the range from around one to twenty minutes, and at a predetermined UVA intensity of around 1.0 to 40.0 mw/cm$^2$. In some embodiments, the UVA radiation has a predetermined intensity in a range from 1.0 to 5 mw/cm$^2$. In some embodiments, a beam intensity or power of 3.0 mw/cm$^2$ is used, providing a total dose over a five minute treatment period at the incident surface of the eye equal to 0.9 J/cm$^2$. A larger or smaller dose is provided in alternative examples, based on the type and size of the incision or wound. As used herein, the terms "UVA intensity", "beam intensity", "beam power", and "power" are used interchangeably and are generally measured by watts per square meter, milliwatts per square centimeter, or a variation thereof.

In some embodiments, the combination of a photosensitizer such as riboflavin monophosphate and UVA light produces collagen cross-linking in eye tissue such as corneal tissue. In some embodiments, the method comprises applying the photosensitizer solution containing both riboflavin and iodide ion along with UVA light at a selected intensity and time period to an ocular wound area, thereby cross-linking across the wound in order to seal the wound. In some embodiments, the iodide ion breaks down hydrogen peroxide produced by the process, thereby creating more oxygen for cross-linking. In some embodiments, cross-linking across the wound improves sealing efficacy. In some embodiments, cross-linking across the wound reduces toxicity by avoiding or reducing formation of peroxides and other destructive forms of reactive oxygen species (ROS). In some embodiments, addition of a fibrin glue or the like to the solution further enhances the process by helping to hold opposing tissue portions of the wound together during the photochemical treatment, so that cross-links are more readily formed.

One problem with current photochemical cross-linking treatment using riboflavin as a sensitizing agent is that oxygen is consumed during cross-linking and the rate of consumption may exceed the normal reoxygenation diffusion rate, so that the cornea remains hypoxic. In some embodiments, the triplet riboflavin molecules created during photochemical therapy either forms singlet oxygen created in a Type II reaction or hydrogen peroxide by a Type I reaction. Under conditions of subnormal oxygen availability (less than 5 mm Hg of O2), the Type I hydrogen peroxide reaction predominates. In some embodiments, iodide ion is a hydrogen peroxide reducing agent. In some embodiments, iodide ion acts to convert hydrogen peroxide into water and oxygen. In some embodiments, iodide ion mediated conversion of hydrogen peroxide into water and oxygen provides a new source of oxygen for singlet oxygen production. In some embodiments, iodide ion mediated conversion of hydrogen peroxide into water and oxygen reduces the toxic levels of hydrogen peroxide and hydroxyl ions. It is also known that as little as 1 micromolar hydrogen peroxide can stop the proliferation of living cells. In some embodiments, iodide ion mediated conversion of hydrogen peroxide into water and oxygen enhances, promotes or maintains proliferation of living cells. In some embodiments, the addition of iodide ion to the solutions used during photochemical cross-linking has the simultaneous effect of reducing toxicity and improving singlet oxygen production.

In some embodiments, sodium iodide is used as the iodide ion for photochemical cross-linking. Although other forms of iodide ion are acceptable. In some embodiments, iodate ion (IO3-) is administered with a reducing agent, thereby producing the iodide ion. In some embodiments, the reducing agent is bisulfite ion (HSO3-). It is known that high levels of iodate ion can destroy the integrity of the retinal pigment epithelium, so caution must be exercised when iodate ion is used to form the iodide ion inside the eye.

In some embodiments, the riboflavin solution comprises riboflavin monophosphate, catalase and/or iodide salts. In some embodiments, the riboflavin solution comprises one or more salts and/or ingredients. In some embodiments, the one or more salts and/or ingredients maintain the intended tonicity and osmolarity of the solution. In some embodiments, the solution comprises sufficient iodide ion and/or catalase to decompose 500 micromolar hydrogen peroxide within five minutes. In some embodiments, the solution comprises sufficient iodide ion and/or catalase to decompose 500 micromolar hydrogen peroxide within four minutes. In some embodiments, the solution comprises sufficient iodide ion and/or catalase to decompose 500 micromolar hydrogen peroxide within three minutes. In some embodiments, the solution comprises sufficient iodide ion and/or catalase to decompose 500 micromolar hydrogen peroxide within two minutes. In some embodiments, the solution comprises sufficient iodide ion and/or catalase to decompose 500 micromolar hydrogen peroxide within one minute. In some embodiments, the solution comprises sufficient iodide ion and/or catalase to decompose 400 micromolar hydrogen peroxide within five minutes. In some embodiments, the solution comprises sufficient iodide ion and/or catalase to decompose 400 micromolar hydrogen peroxide within four minutes. In some embodiments, the solution comprises sufficient iodide ion and/or catalase to decompose 400 micromolar hydrogen peroxide within three minutes. In some embodiments, the solution comprises sufficient iodide ion and/or catalase to decompose 400 micromolar hydrogen peroxide within two minutes. In some embodiments, the solution comprises sufficient iodide ion and/or catalase to decompose 400 micromolar hydrogen peroxide within one minute. In some embodiments, the solution comprises sufficient iodide ion and/or catalase to decompose 300 micromolar hydrogen peroxide within five minutes. In some embodiments, the solution comprises sufficient iodide ion and/or catalase to decompose 300 micromolar hydrogen peroxide within four minutes. In some embodiments, the solution comprises sufficient iodide ion and/or catalase to decompose 300 micromolar hydrogen peroxide within three minutes. In some embodiments, the solution comprises sufficient iodide ion and/or catalase to decompose 300 micromolar hydrogen peroxide within two minutes. In some embodiments, the solution comprises sufficient iodide ion and/or catalase to decompose 300 micromolar hydrogen peroxide within one minute. In some embodiments, the solution comprises sufficient iodide ion and/or catalase to decompose 200 micromolar hydrogen peroxide within five minutes. In some embodiments, the solution comprises sufficient iodide ion and/or catalase to decompose 200 micromolar hydrogen peroxide within four minutes. In some embodiments, the solution comprises sufficient iodide ion and/or catalase to decompose 200 micromolar hydrogen peroxide within three minutes. In some embodiments, the solution comprises sufficient iodide ion and/or catalase to decompose 200 micromolar hydrogen peroxide within two minutes. In some embodiments, the solution comprises sufficient iodide ion and/or catalase to decompose 200 micromolar hydrogen peroxide within one minute. In some embodiments, the solution comprises sufficient iodide ion and/or catalase to decompose 100 micromolar hydrogen peroxide within five minutes. In some embodiments, the solution comprises sufficient iodide ion and/or catalase to decompose 100 micromolar hydrogen peroxide within four minutes. In some embodiments, the solution comprises sufficient iodide ion and/or catalase to decompose 100 micromolar hydrogen peroxide within three minutes. In some embodiments, the solution comprises sufficient iodide ion and/or catalase to decompose 100 micromolar hydrogen peroxide within two minutes. In some embodiments, the solution comprises sufficient iodide ion and/or catalase to decompose 100 micromolar hydrogen peroxide within one minute. In some embodiments, the solution comprises sufficient iodide ion and/or catalase to decompose 20 micromolar hydrogen peroxide within five minutes. In some embodiments, the solution comprises sufficient iodide ion and/or catalase to decompose 20 micromolar hydrogen peroxide within four minutes. In some embodiments, the solution comprises sufficient iodide ion and/or catalase to decompose 20 micromolar hydrogen peroxide within three minutes. In some embodiments, the solution comprises sufficient iodide ion and/or catalase to decompose 20 micromolar hydrogen peroxide within two minutes. In some embodiments, the solution comprises sufficient iodide ion and/or catalase to decompose 20 micromolar hydrogen peroxide within one minute. In some embodiments, the solution is lyophilized. In some embodiments, lyophilization of the solution increases the stability of the solution. In some embodiments, lyophilization of the solution increases the stability of the solution for transport. In some embodiments, lyophilization of the solution increases the stability of the solution for storage. In some embodiments, the lyophilized riboflavin solution is mixed with a solution of hydrogen peroxide in the range of 100-500 micromolar to produce additional oxygen prior to use.

In some embodiments, the riboflavin solution further comprises catalase enzyme. In some embodiments, the riboflavin solution does not comprise an iodide ion. In some embodiments, catalase enzyme is used in place of iodide ion in the riboflavin solution. Catalase is often a large molecule with a molecular weight of about 250,000 and its diffusion into the stroma is often very slow. In some embodiments, the iodide ion is a better stromal catalyst for hydrogen peroxide decomposition than catalase. Also, in the presence of nitric oxide, catalase is rendered inactive but iodide ion continues to decompose hydrogen peroxide. In some embodiments, the catalase is inactivated by the addition of nitric oxide.

In some embodiments, additional oxygen for promoting cross-linking is provided before or during the wound sealing or welding procedure by adding drops of oxygen saturated aqueous tear solution to the wound area or surrounding areas of the eye. In some embodiments, these drops are added in a controlled quantity significantly less than standard tear solution drops. In some embodiments, the tear solution is saturated with oxygen. In some embodiments, an ophthalmic or artificial tear solution applied to the wound further comprises a concentration of iodide ion. In some embodiments, the ophthalmic or artificial tear solution applied to the wound comprises sodium iodide. In some embodiments, sodium iodide is in the range from 0.1 to 130 mmol.

In some embodiments, the tear solutions are pre-oxygenated at a high oxygen partial pressure. In some embodiments, the high oxygen partial pressure is at least about 155 mm Hg partial pressure. In some embodiments, the high oxygen partial pressure is at least about 175 mm Hg partial pressure. In some embodiments, the high oxygen partial pressure is at least about 200 mm Hg partial pressure. In some embodiments, the high oxygen partial pressure is at least about 250 mm Hg partial pressure. In some embodiments, the high oxygen partial pressure is at least about 300 mm Hg partial pressure. In some embodiments, the high oxygen partial pressure is at least about 350 mm Hg partial pressure. In some embodiments, the high oxygen partial pressure is at least about 400 mm Hg partial pressure. In some embodiments, the high oxygen partial pressure is at least about 500 mm Hg partial pressure. In some embodiments, the high oxygen partial pressure is at least about 600 mm Hg partial pressure. In some embodiments, the high oxygen partial pressure is at least about 700 mm Hg partial pressure. In some embodiments, the high oxygen partial pressure is at least about 750 mm Hg partial pressure. In some embodiments, the high oxygen partial pressure is at least about 760 mm Hg partial pressure.

In some embodiments, the tear solution comprises one or more lipid or oil-based fluids. In some embodiments, the one or more lipids or oil-based fluids are pre-oxygenated at high oxygen partial pressures (150-760 mm Hg) for topical application to the cornea. In some embodiments, the oil is a perfluorocarbon or a silicon based oil approved for in vivo use in humans, or a mineral or vegetable oil of sufficient purity for human consumption. In some embodiments, the solution is an emulsion of oils approved for in vivo use in humans, with the aqueous portion of the emulsion containing catalase and/or iodide ion in sufficient quantity to decompose 20 micromolar of hydrogen peroxide within one minute. In some embodiments, the one or more lipids or oil-based fluids are a synthetic oil perfluorodecalin. In some embodiments, the synthetic oil perfluorodecalin carries 100 times more oxygen per volume than an aqueous saline solution. In some embodiments, the oxygenation of the tear solution is accomplished by bubbling oxygen through the solution or by applying high-pressure oxygen mixtures to the solution. For example, bubbling 50% oxygen 50% nitrogen solution through the oil results in an oil with a partial pressure of about 380 mm Hg oxygen.

In some embodiments, the light source 16 in FIG. 1 is a lamp, light-emitting diode, or laser diode. In some embodiments, the lamp, light-emitting diode, light-emitting diode, or laser diode has an output wavelength in both UVA and violet/blue visible light ranges. In some embodiments, the lamp, light-emitting diode or laser diode has filters selectively positioned in the light path to switch between UVA and violet/blue visible light ranges during the wound sealing or welding procedure. In some embodiments, the range of UVA/blue wavelength is about 320 nm to about 475 nm. In some embodiments, the range of UVA/blue wavelength is about 300 nm to about 500 nm. In some embodiments, a UVA/blue wavelength range of about 330 nm to about 470 nm is provided by the light source. In some embodiments, range of filters for UVA treatment allows selection of excitation energy in the UVA band around 365 nm. In some embodiments, the range of blue light treatment is about 400 to about 500 nm. In some embodiments, the range of blue light treatment is about 400 to about 470 nm. In some embodiments, the UVA treatment range is about 300-450 nm. In some embodiments, the UVA treatment range is about 350-400 nm. In some embodiments, the UVA treatment range is about 360-370 nm. In some embodiments, the violet/blue treatment range is about 380-500 nm. In some embodiments, the violet/blue treatment range is about 400-450 nm. In some embodiments, the violet/blue treatment range is about 400-410 nm.

In some embodiments, a light source wavelength is inversely proportional to light source intensity. In some embodiments, a potential advantage of the 405 nm wavelength is the option to use less intense light to accomplish the same amount of cross-linking. The production of singlet oxygen by excited riboflavin triplet molecules is related to the number of incident photons, not the energy of the photons. Riboflavin is excited at both 365 nm and 405 nm to its higher energy states. By the formulation $E=h\nu$ it is determined that a 405 nm photon is 10% less energetic than a 365 nm photon, and that to have equivalent stoichiometric reactions at 405 nm and 365 nm the incident UVA light fluence is reduced to 90% of the blue light value. In some embodiments, there is some advantage in applying UVA light for a first time period, followed by blue light for a successive time period.

In some embodiments, another feature of the blue light option for excitation energy is that the lower absorption of blue light by riboflavin in the anterior cornea translates into less oxygen consumption in the anterior stroma. In some embodiments, lower absorption produces better reoxygenation of the posterior stroma.

Figure 3:
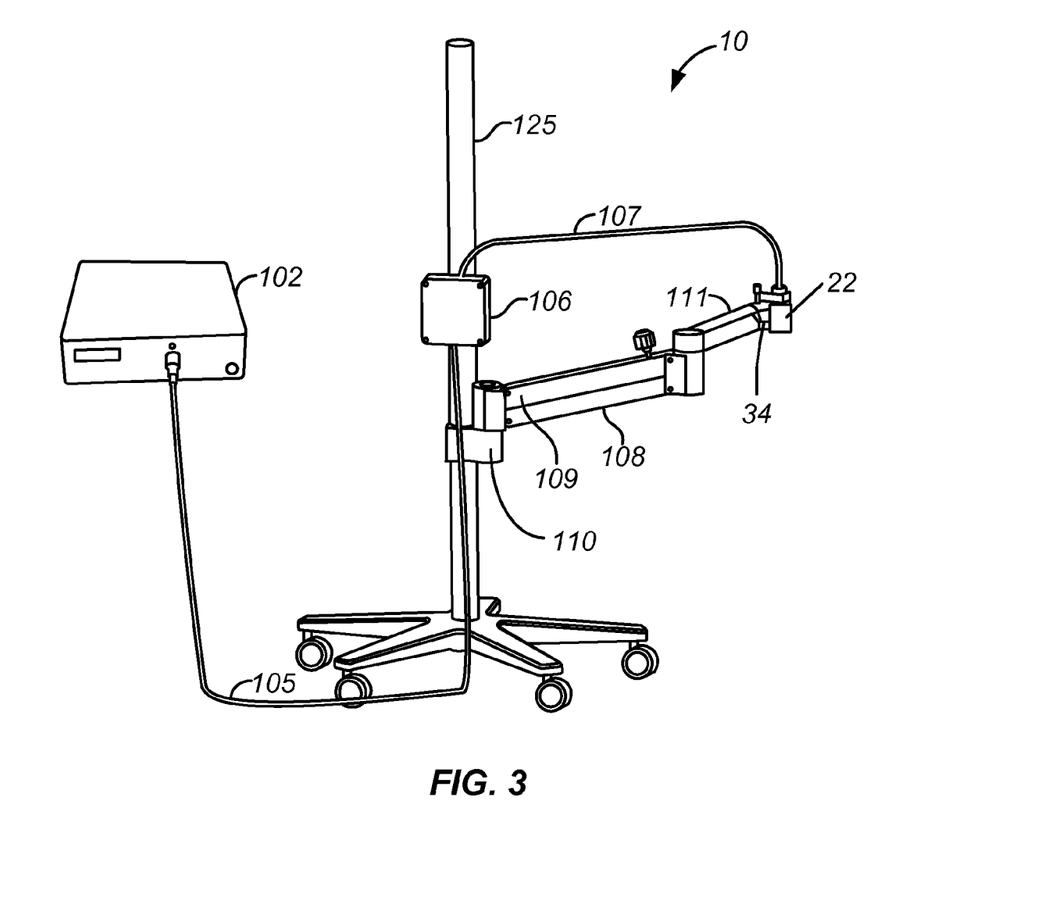
FIG. 3 is an exemplary perspective view of a phototherapy device including an optical treatment head as in FIG. 1 for applying a light beam of a selected UVA frequency to a patient's eye according to some embodiments of the disclosure.
Figure 4:
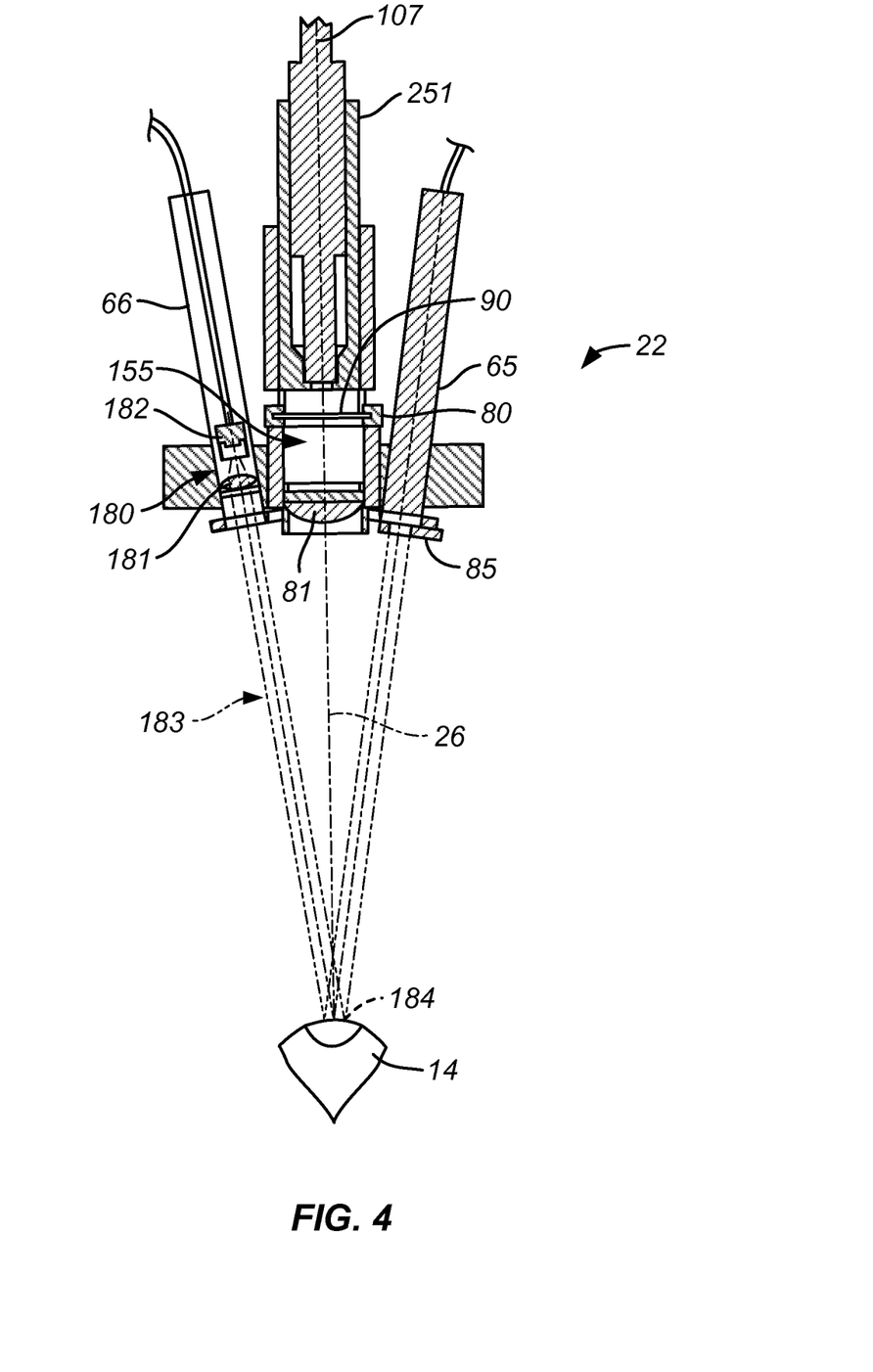
FIG. 4 is a cross sectional view of an exemplary optical treatment head in the system of FIGS. 1 to 3 positioned at a selected working distance from the eye according to some embodiments of the disclosure.

FIG. 3 illustrates one possible embodiment of a phototherapy treatment system including components of FIG. 1 which, in some embodiments, is used for providing UVA or violet/blue visible light irradiation of the wound area. FIG. 4 illustrates one embodiment of optical treatment head 22 in more detail. The treatment system of FIGS. 3 and 4 is described in more detail in co-pending application Ser. No. 13/034,488 of the same applicant filed on Feb. 24, 2011, the entire contents of which are incorporated herein by reference.

As shown in FIGS. 1 and 3, the system 10 comprises an illumination source unit 102 and an optical treatment head 22. In some embodiments, the optical treatment head 22 receives a radiation output signal from the source unit 102 via a first flexible elongate light guide or optical cable 105 connected to the intensity adjustment module 106, and a second flexible light guide 107 extending from module 106 to the treatment head. In some embodiments, the optical treatment head 22 is mounted on an articulated arm assembly or adjustable mounting device 108, and the arm assembly 108 is adjustably mounted on a support stand 125 via mounting device 110 for adjustment of distance of the optical head from a patient's eye. Arm assembly 108 has a first arm 109 slidably mounted at one end on the stand 125, and a second arm 111 pivotally mounted at the end of arm 109. In some embodiments, each arm is locked in position when the optical treatment head 22 at the end of arm 111 is at a desired position relative to a patient's eye. In some embodiments, optical treatment head 22 is secured to the end of arm 111 via swivel joint 34 for angular adjustment relative to the eye. In some embodiments, the intensity adjustment module or unit 24 is also mounted on stand 125. The illumination source unit 102 is shown separate from the stand but, in some embodiments, is mounted on stand 125. In some embodiments, illumination source unit 102 and intensity adjustment module 106 are combined in a single housing. In some embodiments, illumination source unit 102, intensity adjustment module 106 and processor module 28 are combined in a single housing.

In some embodiments, the system is monocular and has a single optical treatment head 102 used to treat one eye at a time. In some embodiments, the system further comprises a second optical treatment head. In some embodiments, the system is used for simultaneous or bilateral treatment of both eyes. Although the system in FIG. 3 has only one treatment head, two treatment heads 22 is in alternative embodiments for treating both eyes simultaneously when wounds are present in both eyes, for example after surgeries in both eyes. In some embodiments, the illumination source unit 102 further comprises a light source 16. In some embodiments, the illumination source unit 102 further comprises a wavelength control filter 18. In some embodiments, the illumination source unit 102 further comprises a light source 16 and a wavelength control filter 18. In some embodiments, the light is directed from the light source 16 through control filter 18 and into the light guide 105/107. In some embodiments, the light guide 105/107 is a liquid light guide or fiber optic bundle.

It will be understood that FIG. 3 illustrates an example of many possible alternative mechanical mounting and adjustment systems which in some embodiments is used to support the optical treatment head at an adjustable position relative to the patient's eye, and the systems and methods described herein are not limited to this example.

In some embodiments, the optical treatment head 22 is illustrated in more detail in FIG. 4. The optical treatment head 22 is also described in more detail in co-pending U.S. application Ser. No. 13/034,488 referenced herein. In some embodiments, light guide 107 terminates at the input of optical projection system 155 that incorporates reticle holder 80 and projection optic or lens 81. In some embodiments, the projection lens 81 is a 12.7 mm diameter lens with a 25 mm focal length. In some embodiments, projection optic or lens 81 projects light according to the pattern on a slide. In some embodiments, projection optic or lens 81 projects light according to the pattern on reticule 90 mounted in reticule holder 80 at a distance of 75 mm with a magnification factor of 3.

In some embodiments, as disclosed herein, the system comprises a kit 30 of slides or masks 90 that offer various circular spot sizes, elliptical shapes on various axes, annular shapes, half moon shapes and horizontal and vertical slit shapes, some of which are illustrated by way of example in FIG. 2. In some embodiments, a projection slide selected from the kit 30 of alternative projection slides is inserted in reticule holder 80 and controls the treatment beam size and shape. In some embodiments, the mask or slide selection is based on the wound size and shape. In some embodiments, the mask or slide is selected such that the beam covers the entire wound area. In some embodiments, the kit 30 comprises slides or masks with different size openings for different wound shapes and sizes.

In some embodiments, an aiming or positioning apparatus 65, 66 is provided in optical treatment head 22 to assist an operator in positioning the projection optic or lens 81 at a desired working distance from the cornea. In some embodiments, the aiming devices 65, 66 are laser diodes angled towards one another so that the beams from the two diodes cross at the desired working distance from the patient's eye. In some embodiments, the distance of optic 81 from the cornea is determined to be equal to the desired working distance when the two aiming beams from laser diodes 65 and 66 coincide with each other as a single spot on the patient's eye. In some embodiments, in an alternative positioning apparatus, as illustrated in FIG. 4, only one laser diode 65 is used which centers on the cornea at the desired working distance from the optical head, which is three inches in an example. In some embodiments, an optical assembly 180 comprising a short focal length lens 181 and a photodiode 182 is oriented to receive maximum reflected light from the surface of the eye when the treatment head is at the desired distance from the eye. In some embodiments of this configuration, when the laser diode 65 is pulsed, the return signal 183 from the first surface or corneal surface 184 is at a maximum when the distance is three inches from the cornea to the optical head.

In some embodiments, light collected by photodiode 182 is connected to output 186 which in turn is connected to processor module 28 (see FIG. 1). In some embodiments, the optical assembly focuses the reflected beam from the laser pulse to the active sensing portion of the photodiode, and any off-axis radiation does not hit the sensing portion of the photodiode. In some embodiments, the operator moves the assembly up and down until the photodiode reading is a maximum. In some embodiments, the maximum photodiode reading occurs at the selected working distance from the center of the aiming beam of the laser diode. In some embodiments, the working distance from the center of the aiming beam is three inches. In some embodiments, the apparatus (positioning apparatus and focal length of projection optic) is modified to provide for different working distances. In some embodiments, the different working distances provide a more accurate method for positioning the optical head at a predetermined distance relative to the patient's eye.

In some embodiments, a separate red light source or a red light source built into the optical treatment head is used in conjunction with UVA/blue light wound sealing treatment as disclosed herein. In some embodiments, use of the red light source promotes sealing and healing, as described in application Ser. No. 13/034,488 referenced above.

In some embodiments, a combination of topical fluids is applied to the eye to promote cross-linking. In some embodiments, a combination of topical fluids is applied to the eye to provide more oxygen. In some embodiments, a combination of topical fluids applied to the eye together with UVA and/or blue light directed to a surgical or traumatic wound in the eye are used to seal or weld a wound. In some embodiments, the methods disclosed herein are used for tissue welding or sealing various types of surgical and non-surgical ocular wounds, including LASIK flap sealing. In some embodiments, the methods further comprise pre treatment of the wound surfaces to enhance tissue welding by cross-linking. In some embodiments, a flap is cut with a microkeratome and amines on the exposed surfaces are protected by adding a mildly acidic solution around the edge. In some embodiments, this changes the amine into amine salts with amine groups. In some embodiments, amine salts with amino groups are converted to aldehydes by the UVA/riboflavin treatment. In some embodiments, conversion of the amine salts to aldehydes by the UVA/riboflavin treatment produces spontaneous cross-linking, thereby resulting in a tissue-tissue seal.

In some embodiments, the tissue surfaces are treated in some cases to have accessible chemical groups helpful for cross-linking. For example by creating some exposed carbon atoms/radicals by surface pretreatment with sodium metal dissolved in ether.

In some embodiments, the ocular wound sealing methods and systems disclosed herein are used for any type of ocular wound sealing in the cornea or sclera, both for surgical wounds and trauma. In some embodiments, the methods and systems disclosed herein are used to treat ocular wounds related to corneal cataract incisions, corneal or scleral lacerations (trauma), relaxing incisions and other surgical wounds resulting from surgery to adjust refractive properties of the cornea, flaps or other incisions from LASIK and other refractive surgeries, scleral incisions, sealing of conjunctival grafts after pterygium surgery, and keratoplasties. In some embodiments, the systems and methods for ocular wound sealing as described herein reduce or adjust astigmatism after cataract or other ocular surgery.

The systems and methods disclosed herein are provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the disclosure and are therefore representative of the subject matter which is broadly contemplated by the present disclosure. It is further understood that the scope of the present disclosure fully encompasses other embodiments that may become obvious to those skilled in the art and that the scope of the present disclosure is accordingly not limited.

We claim:

1. A corneal collagen cross-linking system, the system comprising:
   (a) a supply of a photosensitizer solution that promotes photochemical cross-linking in eye tissue, the photosensitizer solution comprising a hypotonic or aqueous solution containing
      (i) 0.5 wt. % riboflavin, and
      (ii) 0.015 wt. % to 5 wt. % sodium iodide, wherein the iodide is in ionized ($I^-$) form and the solution maintains a basic pH that permits iodide ion to catalytically break hydrogen peroxide into water and oxygen; and
   (b) a light source having an output in a selected UVA or UVA/blue or blue light range.

2. The corneal collagen cross-linking system of claim 1, further comprising an adjustable optical treatment head, the treatment head comprising an optical projector defining an optical axis and configured to project a beam of light in a predetermined UVA or UVA/blue or blue light range along the optical axis.

3. The corneal collagen cross-linking system of claim 1, further comprising a positioning control element for adjusting distance from the eye and the orientation of the optical axis relative to an axis of the eye.

4. The corneal collagen cross-linking of claim 1, further comprising a beam intensity adjustment module for adjusting the light intensity incident on the eye.

5. The corneal collagen cross-linking system of claim 1, further comprising a control module that controls a treatment time period.

6. The corneal collagen cross-linking system of claim 2, wherein the adjustable optical treatment head is adjustable in at least one of an x-axis, a y-axis, and a z-axis.

7. The corneal collagen cross-linking system of claim 1, wherein the UVA or UVA/blue radiation is in a wavelength range from 320 nm to 500 nm.

8. The corneal collagen cross-linking system of claim 1, wherein the UVA radiation is in a wavelength range from 330 nm to 380 nm.

9. The corneal collagen cross-linking system of claim 1, wherein the UVA/blue radiation is in a wavelength range from 400 to 470 nm.

10. The corneal collagen cross-linking system of claim 1, wherein the UVA or UVA/blue radiation is in a wavelength range from 400 to 410 nm.

11. The corneal collagen cross-linking system of claim 1, wherein the basic pH is between 7 and 8.4, not including 7.

12. A corneal collagen cross-linking system, the system comprising:
    (a) a supply of a photosensitizer solution that promotes photochemical cross-linking in eye tissue, the photosensitizer solution comprising a hypotonic or aqueous solution containing
       (i) 0.5 wt. % riboflavin, and
       (ii) 0.015 wt. % sodium iodide, wherein the iodide is in ionized ($I^-$) form and the solution maintains a basic pH that permits iodide ion to catalytically break hydrogen peroxide into water and oxygen; and
    (b) a light source having an output in a selected UVA or UVA/blue or blue light range.

* * * * *